(12) United States Patent
Moloney

(10) Patent No.: US 8,632,810 B2
(45) Date of Patent: Jan. 21, 2014

(54) HYDROCOLLOID COMPOSITION

(75) Inventor: Anthony Moloney, Mt Cotton (AU)

(73) Assignee: Medihoney Pty Ltd., Queensland (AU)

( * ) Notice: Subject to any disclaimer, the term of this patent is extended or adjusted under 35 U.S.C. 154(b) by 1252 days.

(21) Appl. No.: 12/091,897

(22) PCT Filed: Oct. 26, 2006

(86) PCT No.: PCT/AU2006/001597
§ 371 (c)(1),
(2), (4) Date: Aug. 12, 2008

(87) PCT Pub. No.: WO2007/048193
PCT Pub. Date: May 3, 2007

(65) Prior Publication Data
US 2009/0317467 A1  Dec. 24, 2009

Related U.S. Application Data

(60) Provisional application No. 60/730,591, filed on Oct. 26, 2005.

(51) Int. Cl.
*A61L 15/46* (2006.01)
(52) U.S. Cl.
USPC .......................................................... 424/484
(58) Field of Classification Search
None
See application file for complete search history.

(56) References Cited

U.S. PATENT DOCUMENTS

| 4,844,898 A | 7/1989 | Komori et al. |
| 6,956,144 B2 | 10/2005 | Molan |
| 2004/0127826 A1 * | 7/2004 | Caskey .......................... 602/41 |

FOREIGN PATENT DOCUMENTS

| WO | WO 93/19613 | * 10/1993 | ............... A23G 1/00 |
| WO | WO 01/67888 A1 | 9/2001 | |
| WO | WO 02/087644 A1 | 11/2002 | |

* cited by examiner

*Primary Examiner* — Suzanne Ziska
(74) *Attorney, Agent, or Firm* — Foley & Lardner

(57) ABSTRACT

A therapeutic composition is described comprising a particulate dispersion of a hydrocolloid in a low water activity antimicrobial matrix. The composition may also contain any or all of a sequestrant, excipient, carrier and surfactant. The hydrocolloid may be naturally occurring, semisynthetic or synthetic. The invention extends to a method of producing a therapeutic composition. The composition is prepared by mixing a low water activity anti-microbial matrix with hydrocolloid particles at a temperature that will not cause degradation of the matrix. The method may also include the addition of other components such as excipients, sequestrants, carriers and surfactants and other agents. The invention extends to methods for treating a human or animal subject by applying or administering the composition to the subject subject in a therapeutically effective dose.

31 Claims, No Drawings

HYDROCOLLOID COMPOSITION

This application is U.S. National Phase of International Application PCT/AU2006/001597, filed Oct. 26, 2006 designating the U.S., and published in English as WO 2007/048193 on May 3, 2007, which claims priority to U.S. Provisional Application No. 60/730,591, filed Oct. 26, 2005.

FIELD OF THE INVENTION

This invention relates generally to therapeutic compositions and more particularly to compositions including a hydrocolloid dispersed in a low water activity anti-microbial matrix.

BACKGROUND OF THE INVENTION

It is recognised that a satisfactory wound healing agent should create a microenvironment suitable for rapid and effective healing. A wound healing agent desirably has some or all of the following properties, for example: prevents dehydration and scab formation; is sterilizable; absorbs blood and exudate; protects against secondary infection; is non-toxic; does not shed unwanted material into the wound, conforms to anatomical contours, has small bulk, is compatible with other medicaments, and is economical.

Hydrocolloids are water-binding colloids of botanical, animal, microbial or synthetic origin, that have demonstrated some application as wound healing agents. Important properties of hydrocolloids are their ability to thicken, gel and bind water. The water-binding ability of hydrocolloids means that they can absorb exudate from wounds, which in turn makes them suitable for delivering therapeutic substances internally. Current wound dressings of this type are typically comprised of a hydrocolloid such as an alginate. When applied to an exuding or bloody wound, the hydrocolloid hydrates, absorbing the wound fluid, converting to a hydrophilic gel, thereby provides a moist wound environment suitable for wound healing.

The main problem with current hydrocolloid wound dressings is that the moist environment created by the dressing also provides an ideal environment for the growth of bacteria and compromises the healing ability of the dressing. The presence of bacteria often results in breakdown of the hydrocolloid, while excess moisture present in the wound environment can also lead to the breakdown of gel dressings.

SUMMARY OF THE INVENTION

It has now been discovered that particulate dispersions of one or more hydrocolloids in a low water activity anti-microbial matrix are surprisingly effective as wound healing agents with improved efficacy against microbial agents. Accordingly in one aspect, the invention provides compositions comprising a particulate dispersion of at least one hydrocolloid in a low water activity anti-microbial matrix.

Suitable hydrocolloids for incorporation in the compositions of the invention are selected from naturally occurring hydrocolloids, semi-synthetic hydrocolloids and synthetic hydrocolloids.

In some embodiments, the hydrocolloid(s) are selected from naturally occurring polysaccharides, synthetic derivates of naturally occurring polysaccharides, proteinaceous hydrocolloids and synthetic polymers. The hydrocolloid may constitute about 1-50% weight of the composition.

In some embodiments, the low water activity anti-microbial matrix is selected from a saturated sugar solution, one or more honeys, a honey derivative, an artificial honey, or any combination thereof. The low water activity anti-microbial matrix may constitute from about 40 to about 80% weight of the composition.

Suitably, the compositions further include an excipient. The excipient may constitute about 0.6-12% weight of the composition.

Suitably, the compositions further include a sequestrant. The sequestrant may constitute from about 0 to about 3% of the composition.

In some embodiments, the compositions include both an excipient and a sequestrant.

In some embodiments, the compositions include a carrier and optionally at least one surfactant. The carrier may be any compatible, non-toxic substance suitable for delivering the compositions of the invention to a patient. The carrier may be a topical carrier, or a carrier suitable for internal delivery.

The invention is also directed to methods of preparing compositions that comprise a particulate dispersion of at least one hydrocolloid in a low water activity anti-microbial matrix.

Accordingly in a further aspect the invention provides methods for producing a therapeutic composition. These methods generally comprise mixing at least one hydrocolloid with a low water activity matrix at a temperature which is below a temperature that will cause degradation of the matrix. Desirably, the matrix and particles are mixed at low shear.

In some embodiments, the methods further comprise adding one or both of an excipient and sequestrant to the composition.

In some embodiments, the methods further comprise combining a carrier and a surfactant by heating and mixing, cooling the mixture of carrier and surfactant until the mixture has a temperature similar to the temperature of the matrix; and combining the matrix with the carrier and surfactant.

In some embodiments, the methods further comprise sterilisation of the composition.

In some embodiments, the methods may further comprise impregnating a bandage or dressing with the composition for use on a subject.

In yet another aspect the invention provides compositions comprising a particulate dispersion of at least one hydrocolloid in a low water activity anti-microbial matrix prepared by the methods as broadly described above.

The compositions of the current invention are useful wound healing agents for treating external wounds and internal disorders. The compositions may be applied to external wounds, such as wounds of the skin. Alternatively, the compositions may be used as an ingested or internal therapeutic agent.

Accordingly, in still another aspect, the invention provides methods of treating a subject by applying a composition as broadly described above to the site of a wound.

Moreover, due to the usefulness of the aforementioned compositions as wound healing agents, still yet another aspect the invention also extends to the use of a particulate dispersion of a hydrocolloid in a low water activity anti-microbial matrix, in the manufacture of a composition for treating wounds.

DETAILED DESCRIPTION OF THE INVENTION

Typically, once a hydrocolloid is dispersed in an aqueous solution, hydration begins immediately and takes from seconds to several minutes. However, for the compositions of the present invention, the low water activity matrix means that the particulate hydrocolloid dispersion typically does not hydrate unless in response to wound exudate.

The term "water activity" ($a_w$) refers to a measure of the free moisture in a substance and is the quotient of the water vapour pressure of the substance divided by the vapour pressure of pure water at the same temperature. A "low" water activity limits growth of bacteria, and limits the movement of water from one region to another. Water activity is expressed as a scale from 0.0 (bone dry) to 1.0 (pure water). A low $a_w$ is typically less than 0.7, whilst a high water activity is typically greater than 0.8. Higher $a_w$ substances tend to support more microorganisms. Bacteria usually require a water activity of at least 0.91, and fungi at least 0.7.

As used herein, the term "anti-microbial" refers to a drug, agent or process that is inimical to microbes and thus includes "microbiostatic" and "microbiocidal" activities. It shall be understood, therefore, that "anti-microbial" includes within its scope drugs, agents or processes that have one or more activities selected from "fungistatic", "bacteriostatic", "fungicidal" and "bacteriocidal".

By "matrix" is meant a medium comprising a substance or a mixture of substances, in which further substances are embedded, enclosed or contained. A "low water activity anti-microbial matrix" is a matrix that has a low water activity, and has anti-microbial properties. In some embodiments, the $a_w$ of the anti-microbial matrix is less than 0.70, 0.65, 0.6, 0.55 or 0.5.

The term "dispersion" is used herein to refer to any system in which particles of any nature are dispersed in a solid liquid or gas of different composition. A "dispersion", therefore, is a state of subdivision of matter implying that molecules or polymolecular particles (the dispersed phase) are dispersed in a medium (the continuous phase—in this case termed the "matrix"). The particle size of hydrocolloid particles, and particle distribution, are important parameters concerning, for example, the rate of hydration of these particles. The dispersate properties of the hydrocolloid depends upon particle density, matrix density and matrix viscosity. The term "dispersate" refers to a dispersion of finely divided particles of a substance.

As is known in the art, particle density, matrix density and matrix viscosity are interrelated through Stokes' law. Based on Stokes' law, the velocity of fall of a particle in a matrix can be calculated given a known particle density, particle radius, matrix density and matrix viscosity. Alternatively, the equation can be solved for particle radius given a desired velocity of fall. However, calculations based on Stokes' law need to take into account the influence that non-ideal particles (i.e. particles that are not perfectly spherical) may have. For example, non-ideal particles may, due to their shape, further reduce the velocity of fall. Alternatively, the surface of the particles may otherwise interact with the matrix due to the particle's physical and chemical surface properties. Stokes' law is expressed as:

$$V = (2gr^2)(d_1 - d_2)/9\mu$$

where:
V=velocity of fall (m/s);
g=acceleration of gravity (m/s$^2$);
r="equivalent" radius of particle (m);
$d_1$=density of particle (kg/m$^3$);
$d_2$=density of medium (kg/m$^3$); and
$\mu$=viscosity of medium (NS/m$^2$).

The term "particulate", as used in connection with hydrocolloids, relates to minute, discrete particles. In this case, the particles are dispersed in a medium, which is the low water activity antimicrobial matrix. Particle densities, matrix densities, matrix viscosities, and particle radii suitable to form a stable particulate dispersion, in particular a stable hydrocolloid dispersion, are known to the skilled person in the art.

As mentioned, the dispersed hydrocolloid particles hydrate in response to the amount and prevalence of wound exudate. This confers a significant advantage in that the "viscosity" of the composition is substantially maintained, and as such, the anti-microbial matrix is more stable. This property exists because all of the dispersed absorptive hydrocolloid particles are not in direct contact with the wound but are suspended throughout the low water activity matrix.

Dynamic viscosity is the most commonly used form of viscosity, often abbreviated to just viscosity. The viscosity is the tendency of the fluid to resist flow. Increasing the concentration of a dissolved or dispersed substance generally gives rise to increasing viscosity (i.e. thickening), as does increasing the molecular weight of a solute (a dissolved substance).

Viscosity generally changes with concentration, temperature and shear/strain rate in a complex manner, dependent on the hydrated hydrocolloid or hydrocolloids present, as well as the presence of other materials. The proportionality constant of "shear stress" and "shear strain rate" is known as the (dynamic) viscosity ($\eta$). "Fluidity" is the reciprocal of the viscosity ($=1/\eta$).

The relationship between viscosity and concentration is generally linear up to viscosity values of about twice that of water. This dependency means that more extended molecules (e.g. linear polymers) increase the viscosity to greater extents at low concentrations than more compact molecules (e.g. highly branched polymers) of similar molecular weight.

Upon contact with wound secretions, the hydrocolloid particles in the composition come into contact with more "free" moisture and start to swell and transform into a gel that, for example, can expand into the wound and maintain a moist environment. The gel, which is formed in part from the anti-microbial matrix, concomitantly acts as an anti-microbial agent. The gel remains absorbent until the dispersed hydrocolloids are saturated (fully hydrated). Absorptive activity and absorption capacity of the dressing depend on the properties and amounts of the hydrocolloid particles dispersed in the matrix.

As used herein, "gels" refer to liquid-water-containing networks showing solid-like behaviour with characteristic strength, hardness and brittleness dependent on the concentration and structure of the hydrated hydrocolloid(s) present. Hydrated hydrocolloids may display both elastic and viscous behaviour.

Hydrocolloids typically gel when intra- or inter-molecular hydrogen bonding (and sometimes salt formation) is favoured over hydrogen bonding (and sometimes ionic interactions) to water, to a sufficient extent to overcome the entropic cost.

When selecting a hydrocolloid for a particular application, the properties of the hydrocolloid in its hydrated state should be considered depending on the effect required. Relevant properties include: texture, viscosity, flow, water content, stability, stickiness, cohesiveness, resilience, springiness, extensibility, processing time, and process tolerance.

Hydrocolloids interact with water, reducing its diffusion and stabilising its presence. Typically, neutral hydrocolloids are less soluble whereas poly-ionic hydrocolloids are typically more soluble. However, hydration kinetics depend on many factors.

The hydrocolloid may be selected for a range of properties including but not limited to: chemical composition, viscosity, visco-elasticity (gelling properties), particle size, propensity to swell in the presence of acidic solution, and/or ability to remain as a colloidal dispersion following irradiation.

Mixtures of hydrocolloids may show a complexity of non-additive properties. For example, mixtures of hydrocolloids may be used to impart enhanced and unique rheological properties, Mixtures of hydrocolloids, upon hydration, may act in such a way as to affect both viscosity and elasticity of the overall composition. Mixtures of hydrocolloids may act synergistically to increase viscosity or antagonistically to reduce it. A mixture of hydrocolloids may also affect factors such as syneresis, which is the loss of water from a gel by exudation of the liquid component of that gel. These effects are known to those of skill in the art.

Mixtures of hydrocolloids may also comprise a hydrated hydrocolloid in an antimicrobial matrix, thus providing a low-water activity antimicrobial matrix, with a second particulate hydrocolloid dispersed in this matrix to provide a particulate dispersion.

The therapeutic composition is suitable for wound management during all individual healing phases, for example, for the acceleration of wound cleansing, as well as for the promotion of granulation and epithelialization.

The compositions of the present invention, when used as part of a wound dressing, are typically sterilizable, absorb blood and exudate, and do not adhere to the wound surface. As such, the dressing can absorb exudate, detritus, bacteria, and toxic substances from the damaged tissue engaged in wound repair. For example, the wound dressing can draw bacteria away from the wound, helping to protect against wound sepsis. By incorporation of extremely hydroactive hydrocolloids, the dressing has a high absorbency and is thus suitable for heavily exudative wounds. With less heavily exuding wounds, a composition with a lower absorbency hydrocolloid may be preferred.

Upon absorption, surplus contaminated secretions, detritus, and toxic compounds are bound in the matrix. The adsorptive action of the dressing may simultaneously improve the microcirculation in the wounded area, and physiological secretion is stimulated.

The hydrocolloids of the therapeutic composition may be naturally-occurring, synthetic or semi-synthetic. Hydrocolloids may be charged or neutral molecules. Typically, charged hydrocolloids change their structural characteristics with counter-ion type and concentration (including pH and ionic strength effects). Neutral hydrocolloids are also effected by pH and solvate composition (e.g. the presence of other hydrocolloids, proteins and other organic molecules, ions and other charged particles, etc.).

Naturally-occurring hydrocolloids include but are not limited to: botanical, animal and microbial hydrocolloids.

One illustrative, chemically interrelated, class of hydrocolloids is the class of polysaccharides. Polysaccharides can be naturally-occurring (typically of algal, other botanical or microbial origin (fungal, protozoan, bacterial, etc.)), synthetic or semisynthetic. Polysaccharides are classified on the basis of their main monosaccharide components and the sequences and linkages between them, as well as the anomeric configuration of linkages, the ring size (furanose or pyranose), the absolute configuration (D- or L-) and any other substituents present. Certain structural characteristics such as chain conformation and intermolecular associations will influence the physico-chemical properties of polysaccharides. The hydrodynamic volumes (and hence viscosities) of more-extended well-hydrated polysaccharides, (such as for example, alginates and xanthans) increase approximately linearly with molecular weight.

Polysaccharidic hydrocolloids of botanical origin, for example plant/plant seed gums and mucilages (plant exudates and extracts), include hydrocolloids such as: gum tragacanth, an exudate from the leguminous shrub *Astragalus gummifer*; gum arabic, prepared from an exudate from the stems and branches of sub-Saharan (Sahel zone) *Acacia senegal* and *Acacia seyal* (Leguminosae) trees and produced naturally as large nodules during a process called gummosis to seal wounds in the bark of the tree; karaya gum, a gum derived from the dried exudation of the Indian tree *Sterculia urens*; guar gum, a galactomannan extracted from the seed of the leguminous shrub *Cyamopsis tetragonoloba*; cacao pod gum; dammar gum; gum ghatti, (Indian gum) an exudate from the stem of *Anogeissus latifolia*; locust bean gum, a galactomannan extracted from the seed (kernels) of the carob tree (*Ceratonia siliqua*); other mannans (polysaccharides consisting of mannose units), such as manna gum exuded from leaves and bark of *Eucalyptus viminalis;* konjac mannan; a linear polysaccharide composed of mannose and glucose derived from tubers of elephant yam *Amorphopallus konjac*; psyllium seed gum, from the seeds of *Plantago*; quince gum, extracted from the seeds of a deciduous bushy tree, *Cydonia oblonga*; tara gum, a galactomannan gum produced from milled seeds of a shrub species of *Caesalpina*; fenugreek gum, a galactomannan containing gum which comes from the seeds of an annual, *Trigonella foenum-graecum*; aloe gum, a mannan gum extracted from the leaves of *Aloe* species, for example, *A. vera*; chia gum, extracted from the seeds of *Salvia hispanica*, displays exceptional mucilaginous properties at low aqueous concentration; okra gum, extracted from the pods of *Abelmoschus esculentus*; yellow mustard gum, produced from mustard seeds (*Sinapis alba*); tamarind gum, obtained from the seeds of *Tamarindus indica*; carboxymethyl tamarind gum; welan gum, a microbial polysaccharide produced by a species of *Alcaligenes*; sesbania gum, a cold and hot water soluble polymer, classified as a galactomannan polysaccharide, extracted from *Sesbania* (*Sesbania Aculeata*) seeds; cassia gum, a hot water soluble polymer, extracted from *Cassia* (*Cassia Tora*) seeds; and arabinogalactans, for example larch arabinogalactans which are a polysaccharides derived from wood of *Larix occidentalis*.

Further non-limiting examples of polysaccharidic hydrocolloids of botanical, in particular algal origin, include seaweed extracts such as: carrageenans, which are high-molecular-weight polysaccharide prepared by alkaline extraction (and modification) from red seaweed (Rhodophycae), mostly of genus *Chondrus, Eucheuma, Gigartina* and *Iridaea* of which there are three types: iota, kappa and lambda, each having different chemical and functional properties, kappa makes a strong, rigid gel, while iota forms an elastic gel, lambda do not significantly gel, (tara and locust bean gums have also been known to work synergistically with kappa-carrageenan, as well as xanthan gums to increase gel strength and make such gels less prone to syneresis); agar, prepared from the same family of red seaweeds (Rhodophycae) as the carrageenans and commercially obtained from species of *Gelidium* and *Gracilariae*, consists of mixtures of agarose and agaropectin; agar-agar; furcellaran, an extract from the red seaweed *Furcellaria lumbricalis*; alginates, linear unbranched polymers containing β-(1→4)-linked D-mannuronic acid and α-(1→4)-linked L-guluronic acid residues, produced by brown seaweeds (Phaeophyceae, mainly *Laminaria Lessonia* and *Durvillaea*) example of which include sodium alginate, calcium alginate, alginic acid and other semi-synthetic derivatives such as propylene glycol alginate.

Polysaccharidic hydrocolloids may also be of microbial origin. Illustrative examples of hydrocolloids of microbial origin include: gellan, comprised of bacterial exopolysaccharides; scleroglucan, a relatively low molecular weight high viscosity glucan polysaccharide produced by *sclerotium* sp., yielding only glucose on complete hydrolysis; the chemical structure typically consists of β-(1→3)-D-glucose residues with one β-(1→6)-D-glucose side chain every three main residues; pullulan, a neutral glucan with a chemical structure somewhat dependent on carbon source, produced by different strains of *Aureobasidium pullulans*; gum levan, a gum formed by bacteria from sugar; dextran, produced by *Mesenteroides*; xanthan, a polysaccharide with a glucan backbone prepared commercially by aerobic submerged fermentation from *Xanthomonas campestris*; curdlan, a microbial fermentation extracellular polysaccharide; and laminarin, a β-glucan polysaccharide produced by many chromists through photosynthesis. Bacteria derived alginates are also known.

Hydrocolloids may be cellulosic materials, which are also carbohydrate-based structures. Non-limiting examples, including semi-synthetic derivatives, are: cellulose; carboxymethyl β-glucan; carboxymethyl cellulose; cross-linked sodium carboxymethyl cellulose; crystalline sodium carboxymethyl cellulose; hydroxyethyl cellulose; methyl cellulose; and hydroxypropyl cellulose.

Polysaccharidic hydrocolloids may be derived from grasses (botanical origin). Non-limiting illustrative examples include: arabinoxylans, naturally found in the bran of grasses; β-glucans, occurring in the bran of grasses (Gramineae) such as barley, oats, rye and wheat and which consist of linear unbranched polysaccharides of linked β-(1→3)- and β-(1→4)-D-glucopyranose units; non-fermentable cereal gums (for example: corn hull gum); starch flour starch, corn starch, potato starch, etc. Typically, starch consists of two types of molecules, amylose and amylopectin. Both usually consist of polymers of α-D-glucose units. In amylose these are (1→4)-linked, whereas in amylopectin about one residue in every twenty or so is also (1→6)-linked forming branch-points. The relative proportions of amylose to amylopectin and (1→6) branch-points both depend on the source of the starch. Starches may be in the form of modified starches (semi-synthetic derivatives) such as: starch sodium polyacrylate; soluble starch; carboxymethyl starch; dialdehyde starch; and cross-linked dextrans, etc.

Other naturally occurring polysaccharidic hydrocolloids are described in "Polysaccharide Gums from Agricultural Products Processing, Structures, and Functionality", Steve W. Cui (CRC Press 2000).

Semi-synthetic hydrocolloids are hydrocolloids of natural origin that have been modified by further chemical process. Further chemical derivatisation of naturally occurring hydrocolloids can be useful for tuning the chemical and physical properties of naturally occurring hydrocolloids such as solubility, stability, gelling ability, viscosity, etc. Non-limiting examples of semi-synthetic hydrocolloids are hydrocolloids that are copolymers of starch or cellulose, such as starch-acrylonitrile graft copolymer; a starch polyacrylate salt, and sulfuric acid, vinyl sulfonate, methacrylic acid, vinyl alcohol, vinyl chloride copolymers. Other semi-synthetic hydrocolloids include modified guar gums, esterified uronic acid containing polymers such as hyaluronates and alginates, and hyaluronate polyvinyl alcohol blends. Another class of semi-synthetic hydrocolloids are chitosans formed from partial or complete deacetylation of chitin and/or depolymerization.

Synthetic hydrocolloids are chemically synthesised polymers that sometimes have no structural relationships to natural hydrocolloids. Illustrative examples of synthetic hydrocolloids suitable include: polyvinyl pyrrolidone; carboxyvinyl polymers and polyethylene oxide polymers; polymers of methyl vinyl ether and maleic acid and derivatives; polyvinyl alcohol, high molecular weight polyethylene glycols and polypropylene glycols; sodium polyacrylates and polyethylene oxides.

Suitably, hydrocolloids may be proteinaceous. Illustrative examples of various proteinaceous hydrocolloids are: gelatin—prepared by the thermal denaturation of collagen, isolated from animal skin, cartilage, ligaments, tendons and bones, and also extracted, for example, from fish skins; casein; egg albumin; vegetable proteins such as soy derived compounds; whey proteins; and other milk proteins such as caseinate.

Hydrocolloids may be in a neutral, charged, or in a salt form. Non-limiting examples of acidic hydrocolloids, which may or may not be in salt form, are gum arabic, alginates and alginic acid, gum ghatti, xanthan gum, gum karaya, and tragacanth gum. Exemplary neutral gums are guar gum, locust seed gum, and tamarind gum. Suitable counterions, for example metallic counter ions such as $K^+$ and $Na^+$ and the like, are known to those skilled in the art.

The viscosities and gelling properties of different hydrocolloids may be compared and related to each other. For example, it is known that gum arabic has a lower viscosity that gum ghatti which has a lower viscosity than gum karaya; whilst tragacanth gum, xanthan gum and alginates have relatively high viscosities.

In addition to their rheological properties, hydrocolloids may possess other advantageous properties. For example, gum arabic is known to inhibit crystallisation of sugar from sugar syrups. Other hydrocolloids are known to have a laxative effect such as agar-agar, which stimulates peristaltic action. Yet other hydrocolloids have been traditionally used for the treatment of diarrhea, for example, gum tragacanth.

The low water activity antimicrobial matrix may be an admixture of known ingredients, dissolved in an aqueous solution. The matrix may be a naturally occurring substance or may be a combination of synthetic, semi-synthetic and naturally occurring substances.

Examples of low water activity antimicrobial matrices include super saturated sugar solutions, saturated sugar solutions derived from natural sources and naturally occurring substances such as honey.

Illustrative examples of sugars are mannose, glucose, fructose, xylose, galactose, ribose, dextrose, arabinose, trehalose, maltose, maltulose, maltodextrin, sucrose, lactose, cyclodextrins, raffinose, stachyose and lactulose. Other suitable sugars are known to those skilled in the art.

Non-limiting examples of sugar solutions derived from natural sources are birch syrup, corn syrup, sorghum syrup, maple syrup, palm sugar, fruit extracts—e.g. Lo Hun, and rice syrup.

In addition to sugars, the therapeutic composition may include other polyhydroxylated sugar like compounds such as cyclitols. Non-limiting examples of cyclitols include inositol, sorbitol, xylitol, and mannitol.

Optionally, additional polyhydroxylated compounds are included in the therapeutic compositions, as required, for further therapeutic benefit and/or for their rheological properties. Non-limiting examples of other suitable polyhydroxylated compounds include glucosamines; galactosomines; mannosamines; lactosamines; glycosaminoglycans such as chondroitins, dermatans, heparans, heparins, heparinoids, hyaluronic acids and hyaluronates; glycoalkaloids or glycosteroids such as solasodine compounds; glycyrrhizic acids; and either high and low molecular weight chito-oligomers such as chitins and chitosans. By way of example, aminosugars have demonstrated therapeutic benefit as anti-inflammatory agents, hyaluronic acids as wound healing agents, heparins as anticancer agents and anticoagulants, and chitosans as hydrocolloidal wound healing agents. Suitably, the polyhydroxylated compound is a homeostatic agent.

Super saturated sugar solutions have a very low water activity. Honey, for example, has virtually no "available" water. As such, bacteria cannot grow in honey because there is not enough free water for the bacteria to use (it is bound to the sugars and enzymes in the honey). Depending on its water content, temperature, floral source and other factors, the water activity of undiluted honey typically varies between about 0.50 and 0.65.

Suitably, the low water activity antimicrobial matrix includes honey or a honey derivative. The honey component of the composition may include a combination of one or more honeys selected for their therapeutic properties. In some embodiments, the honeys are derived from the Australian or New Zealand *Leptospermum* species. The honeys may include, for example, a combination of two or more honeys selected for differing but preferably complementary physiological/therapeutic action including those with peroxide and non-peroxide anti-microbial activity. This combination may ensure a broad spectrum of anti-microbial activity. There are many known types of honey. Examples are identified in publications such as *Honey and Pollen Flora, Clemson A, INKATA PRESS Pty Ltd, Melbourne,* 1985 and similar reference works. Honeys may be selected on the basis of the presence of flavonoids which may act as an anti-oxidant, e.g. resulting in inflammation reduction. Honeys may also be selected for the presence of growth factors which can assist with granulation, epithelialization and the growth of new tissue to ensure a progressive and satisfactory healing process. The honeys may also be selected on the basis of the presence, or levels, of physiologically active compounds including but not limited to flavonoids, alkaloids, growth regulators and compounds that cause stimulation of TNF-alpha release. Honey may also be selected based on the presence of aromatic and phenolic components.

The therapeutic compositions may comprise a carrier as an optional ingredient. The carrier may be any pharmaceutically compatible substance suitable for delivering the compositions of the invention to a patient. One suitable class of carriers is waxes. The term "wax" typically refers to a solid, semi-solid, and occasionally liquid material derived from animal (e.g. beeswax and lanolin), plant (e.g. palm tree, candelilla, cotton and hemp wax) mineral/fossil/oil (e.g. montan wax, rod wax, and microcrystalline wax) or synthetic origin (e.g. polyethylene wax, ethylene copolymer wax, carbowax, halogenated hydrocarbon waxes, and synthetic mono esters of fatty acids (fatty esters)). The types of waxes listed above do not necessarily form a chemically homogeneous group. A wax may made up of various substances including: hydrocarbons (normal or branched alkanes and alkenes), ketones, diketones, primary and secondary alcohols, aldehydes, sterol esters, fatty acids, terpenes and monoesters of fatty acids, typically with at least one long, or very long carbon chain (from 12 up to about 38 carbon atoms). In addition to mixtures, waxes may also be comprised of a single chemical compound, for example, a substantially pure ester of fatty acid (a fatty ester). Illustrative non-limited examples of waxes are: beeswax; Chinese wax; shellac or lac wax; cetyl palmitate (spermaceti); mixtures based on jojoba extracts; epicuticular wax; fatty alcohols; fatty esters, carnauba wax; Jojoba liquid wax; Montan wax; candelilla wax; Japan wax; and rice bran oil.

In some embodiments, the wax has a melting range of from about 37 to 43° C. In illustrative examples of this type, the wax has a melting point of 40° C. The melting point of the wax is typically selected so that the composition is substantially non-running at the body temperature of a patient, usually around 37° C. in a person but may be higher in domestic animals. Optionally, waxes with higher melting points are selected based on the body temperature of the animal or animals to be treated. One means of assessing whether the composition is non-running is to place a sample on a slope, preferably at 45°, and demonstrate that the sample does not freely flow down the incline at the temperature at which a wound would be healed, usually around 37° C. However, it is recognised that due to inflammation, environment, fever and other disease states, the temperature at which the wound is to be healed may vary from that of a normal healthy body temperature. As mentioned before, the body temperature of other animals may vary from that of humans.

The present invention is not dependent on any particular waxes and extends to any and all waxes with the desired properties irrespective of source. In some embodiments, the wax is a mixture of higher melting point and lower melting point wax substances in order to provide a mixture of waxes that has a melting point in the range of 37-45° C. As such, alternative or additional ingredients may include any fatty ester or fatty alcohol, or mixtures of fatty esters and fatty alcohols, that satisfies the condition of having a relatively narrow melting range around 40° C.

An example of a suitable wax is myristyl myristate. This is a wax with a low melting point, usually in the range of from about 37 to about 43° C. It also has good skin-softening and lubricating properties.

Another optional ingredient is a surfactant. Surfactants are materials that facilitate and accentuate the emulsifying, wetting and other surface-modifying properties of substances. For example, a surfactant may be a substance that when dissolved in an aqueous solution reduces the surface tension between it and another liquid. Typically, surfactants are organic molecules that contain a hydrophilic group at one end and a lipophilic group at the other. Suitably the surfactants are non-ionic, low irritant and mild chemicals. A suitable surfactant is an ethoxylated triglyceride such as ethoxylated sweet almond oil or a derivative thereof. Ethoxylated castor oil or ethoxylated evening primrose oil, are also suitable surfactants.

Yet another optional ingredient is an excipient. An excipient is an inactive or inert substance which is added to a formulation, usually to provide for example: stability, bulk, form, or consistency. An example of a suitable excipient is calcium sulphate dihydrate.

Still another optional ingredient is a sequestrant. A sequestrant is a chemical substance that promotes sequestration, which is the inhibition or prevention of normal ion behaviour by combination with added materials. Sequestration especially relates to the prevention of metallic ion precipitation from solution by formation of a coordination compound. For example, sequestrants are chemicals that promotes sequestration, for example, that combine with polyvalent metal ions to form a soluble metal complex. An example of a suitable sequestrant is tetra sodium pyrophosphate.

In a preferred method of manufacture of the present therapeutic compositions disclosed herein, a low water activity antimicrobial matrix is mixed with hydrocolloid particles substantially at room temperature (about 20 to 25° C.). Optionally, the low water activity antimicrobial matrix is slightly heated, for example, to reduce viscosity of the matrix and to increase its flow characteristics and lability. Desirably, the temperature to which the matrix is heated does not exceed temperatures that will degrade the matrix. Suitably, if the matrix is heated, the temperature of the matrix does not exceed about 40° C. In some embodiments, the temperature of the matrix during the manufacturing process is about 15 to 30° C., 18 to 27° C., or 20 to 25° C. In a specific embodiment, the temperature is 25° C. Temperatures at which matrices, such as honey, degrade, are known to those skilled in the art. In some embodiments, the hydrocolloid(s) are added to the matrix, as the matrix is being stirred. Optionally, an excipient and sequestrant are added to the mixture. If desired, the matrix may be heated gently to allow for a reduction of the viscosity of the matrix to aid dispersion of the hydrocolloid throughout the matrix. Similarly, continuous mixing of the matrix further enables even dispersion of the hydrocolloid throughout the matrix. In some embodiments, the hydrocolloid particles are dispersed in the matrix by mixing with low shear, for example, to minimise hydration of the hydrocolloid particles.

The dispersion of hydrocolloid particles in the low water activity antimicrobial matrix with low shear can be accomplished, for example, with conventional low shear mixers. Low shear mixing is a mixing technique whereby the liquid components are mixed primarily by rolling and stirring in a mixing chamber of relatively large volume. Power loss and mechanical energy transfer in the form of heat are generally quite low. Examples of a conventional low shear mixer include the Peerless or Hallmark Brand mixer, a horizontal blender, pin-type mixer and a low-shear planetary mixer. Optionally, the low shear mixer may be a high torque low shear mixer. In specific embodiments the low shear is from about 0.1 to 1750 rpm, 5 to 550 rpm, 10 to 250 rpm, or 20 to 150 rpm.

Optionally, a wax and surfactant may also be added to the therapeutic composition. In these circumstances, separately, wax and surfactant are heated while being mixed with each other until both are fully melted. The temperature in this process may typically reach between 50-60° C. In some embodiments, the wax/surfactant mixture is equilibrated to the temperature of the matrix, at which time it is added to the matrix with high shear mixing until homogeneity is reached. The mixing period may be relatively brief. The mixed composition may then be cooled and packed for distribution.

In some instances, particularly if the matrix is of natural or is of naturally derived sources, the composition may be sterilised, for example, to inactivate spores, such as *Clostridium* sp spores, and to provide an associated reduction in bioburden levels. An illustrative method of sterilisation is by gamma irradiation, usually at levels between 25-35 kGy.

In representative examples, the therapeutic composition may be formulated according to the following proportions:

| Ingredient | Range (% wt/wt) |
| --- | --- |
| low water activity matrix | 50-99% |
| hydrocolloid | 1-50% |
| Excipient | 0-12% |
| Sequestrant | 0-1% |
| Wax | 0-50% |
| Surfactant | 0-15% |

In some embodiments, the low water activity matrix is present in the range of 60-80%, the hydrocolloid is present in the range of 1-50%, the excipient is present in the range of 0.6-12%, sequestrant is present in the range of 0-1%, the wax is in the range of 0-20%, and surfactant is present in the range of 0-7%.

In a further example, the composition may be formulated according to the following proportions:

| Ingredient | Range (% wt/wt) |
| --- | --- |
| Honey or honey derivative | 50-99% |
| Sodium alginate | 1-25% |
| Calcium sulphate dihydrate | 0-12% |
| Tetra sodium pyro phosphate | 0-1% |
| Myristyl Myristate | 0-50% |
| Ethoxylated sweet almond oil | 0-15% |

In some embodiments the matrix is honey and is present in the range of 60-80%, the hydrocolloid is sodium alginate and is present in the range of 1-25%, the excipient is calcium sulphate dihydrate and is present in the range of 0.6-12%, the sequestrant is tetra sodium pyrophosphate and is present in the range of 0-1%, the wax is myristyl myristate and is in the range of 0-20% and the surfactant is ethoxylated sweet almond oil and is present in the range of 0-7%.

It is envisaged that in some embodiments, the present composition may also be used for cosmetic rather than therapeutic purposes. In this case, selection of matrices with clinical characteristics is not essential. Clearly, matrices may also be selected for the treatment of essentially aesthetic problems such as comedones or pimples. Selected matrices in these cases may be bacteriostatic.

Once produced, the composition may be packaged and distributed in any suitable fashion. It may be dispensed into tubes, alternatively it may be formed as part of a wound dressing by impregnation into a wound dressing material. The composition may be packed into individual screw top containers or it may be delivered in sealed capsules or sachets for single use dispensing and treatment. It may be delivered in capsules in a form suitable for human ingestion.

The composition of the present invention has a wide range of applications, and as already noted may be used in both human and veterinary medicine, as well as for human cosmetics. In its simplest form, the composition may be applied topically to a lesion. The frequency of application may be varied to reflect the severity of the condition and the efficacy of the treatment. It is envisaged that an application rate of up to two to three times daily may be of benefit in some circumstances while application every 2-14 days may be suitable in other circumstances where the contact time is prolonged. The composition is preferably of suitable viscosity such that it can be easily dispensed, and can be moulded or pressed into shape using finger pressure to adopt a configuration suitable for a lesion. That shape may be retained while the composition is fixed in position by a support bandage or similar.

The viscosity of the composition may be selected so that the composition is suitable for filling wound cavities. The composition may be beneficially utilised in post surgical wounds, sinus wounds, fistulae, burns, donor sites, infected wounds, pressure ulcers, venous ulcers, diabetic ulcers, trauma injuries, catheter exit sites, dental extraction sockets, fungating/malignant wounds, lesions, ophthalmology and surgical procedures. This list is not comprehensive.

The composition may be beneficially utilised to deliver therapeutic substances internally. The present composition may be applied to mucous membranes and may be dispensed into bodily cavities for the treatment of mucous membranes. The composition may be ingested for beneficial results in some circumstances. The composition may be such that at body temperature, compared to room or storage temperature, it will soften and conform to a wound and surface to which it is applied and will remain in place at temperatures up to 37° and preferably up to 40°.

The nature of the composition makes it practical for bulk manufacture and relatively easy dispensing into packages and containers.

The ingredients of the combination are typically stable, inert, non-irritating and safe to use in therapeutic applications. Further, the composition is such that a stable and homogenous mix of ingredients is achievable within the manufacturing temperature restrictions.

For the management of wounds, the therapeutic composition can be applied either directly to the wound or to a dressing. A thin absorbent dressing with a non/low adhering surface can be used to cover the composition with additional absorbent secondary dressings applied as required. For example when treating a leg ulcer, a composition of the invention is applied to a wound followed by Adaptic (J&J) and a secondary dressing such as Mepilex (Mollnyke). When treating a surgical wound, a layer of a composition of the invention is applied to a wound followed by a film dressing such as Tegaderm (3M). For a deep wound, a ribbon gauze impregnated with a composition of the invention is applied to the wound, which is then covered with an absorbent dressing such as Zetuvit (Hartmann).

The frequency of dressing changes required may depend on how rapidly the composition is being hydrated by exudate. Daily dressing changes are usual during the initial stages of wound healing. More frequent changes may be needed if the composition is being hydrated by a heavily exudating wound. When exudation is reduced, dressing changes can be less regular (2 to 3 days).

The therapeutic composition provides natural debridement of the wound through autolysis so the wound may appear deeper after the initial dressing changes.

It is within the scope of the invention to add other ingredients known to a skilled person to provide compositions with additional characteristics. Further ingredients may include pharmaceutical, veterinary and cosmetic ingredients. Examples of pharmaceutical ingredients include agents such as non-steroidal anti-inflammatories, Cox-2 inhibitors, haemostatic agents, pain treatments such as analgesics, bioflavanoids, ancillary antimicrobial agents, and recombinant activated FVIIa.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the disclosure.

EXAMPLES

TABLE 1

| | | Basic Compositions | | | |
|---|---|---|---|---|---|
| Ex. No. | H1 | LWAM | Sequestrant | Excipient | Other |
| Trial 1 | Na Alg. 2% | Lept. sp. honey 97% | | | 1 |
| Trial 2 | Na Alg. 6% | Lept. sp. honey 91.2 | $Na_4P_2O_7$ 0.8% | $CaSO_4$ 2% | |
| Trial 3 | Na Alg. 10% | honey blend 90% | | | |
| Trial 4 | Na Alg. 15% | honey blend 85% | | | |

The compositions in Table 1 were prepared by mixing honey with hydrocolloid particles with low shear mixing. The temperature of mixing was at room temperature.

TABLE 2

Examples of Hydrocolloids Compositions in a Low Water Activity Antimicrobial Matrix.

| Ex No | Hydrocolloid 1 | Hydrocolloid 2 | LWAM | Sequestrant | Excipient | Carrier | Other 1 | Other 2 |
|---|---|---|---|---|---|---|---|---|
| Ex. 1 | Sodium Alginate: 2% | | Lept. sp honey: 77% | | | Myristyl Myristate: 15% | Ethoxylated sweet almond oil 5% | |
| Ex 2 | Sodium Alginate: 6% | | Lept. sp honey: 71.2% | $Na_4P_2O_7$ 0.8% | $CaSO_4$ 2% | Myristyl Myristate: 15% | Ethoxylated sweet almond oil 5% | |
| Ex 3 | Sodium Alginate: 10% | | honey blend: 70% | | | Myristyl Myristate: 15% | Ethoxylated sweet almond oil 5% | |
| Ex 4 | Sodium Alginate: 15% | | honey blend: 65% | | | Myristyl Myristate: 15% | Ethoxylated sweet almond oil 5% | |
| Ex 5 | Sodium Alginate: 8% | | Lept. sp honey: 72% | | | Myristyl Myristate: 15% | Ethoxylated sweet almond oil 5% | |
| Ex 6 | Sodium Alginate: 8% | | Lept. sp honey: 81% | | | purified lanolin: 10% | | |
| Ex 7 | Sodium Alginate: 8% | | Lept. sp honey: 68% | $Na_4P_2O_7$ 1% | $CaSO_4$ 3% | purified % | | |
| Ex 8 | Sodium Alginate: 8% | | honey blend: 62% | | | purified lanolin: 30% | | |
| Ex 9 | Sodium Alginate: 8% | | honey blend: 42% | | | purified lanolin: 50% | | |
| Ex 10 | Sodium Alginate: 8% | | Honey from genra *Trigona* bee: 91% | | | | | |
| Ex 11 | Sodium Alginate: 8% | | Honey from genra *Austroplebeia* bee: 92% | | | | | |

TABLE 2-continued

Examples of Hydrocolloids Compositions in a Low Water Activity Antimicrobial Matrix.

| Ex No | Hydrocolloid 1 | Hydrocolloid 2 | LWAM | Sequestrant | Excipient | Carrier | Other 1 | Other 2 |
|---|---|---|---|---|---|---|---|---|
| Ex 12 | Sodium Alginate: 8% | | Sat. sugar soln: 92% | | | | | |
| Ex 13 | Sodium Alginate: 8% | | Antibac. honey blend: 92% | | | | | |
| Ex 14 | Sodium Alginate: 8% | | High peroxide antibacterial honey: 92% | | | | | |
| Ex 15 | Sodium Alginate: 8% | | Antibac. honey blend: 92% | | | | | |
| Ex 16 | Sodium Alginate: 8% | | Non-peroxide antibacterial honey: 92% | | | | | |
| Ex 17 | Sodium Alginate: 6% | | Honey from *Meliponula* sp bee: 94% | | | | | |
| Ex 18 | Sodium Alginate: 8% | | Honey from the genra *Trigona* bee: 82% | | | | Sucrose: 5% | Dextrose: 5% |
| Ex 19 | Sodium Alginate: 8% | Chitosan: 2% | Antibac. honey blend: 84% | | | | | Dextrose: 6% |
| Ex 20 | Sodium Alginate: 8% | Chitosan: 6% | Antibac. honey blend: 79% | | | | | Dextrose: 7% |
| Ex 21 | Sodium Alginate: 6% | | Antibac. honey blend: 92% | | | | Opiate: 2% | |
| Ex 22 | Sodium Alginate: 6% | | Antibac. honey blend: 93% | | | | Opiate: 1% | Non-steroidal anti-inflammatory agents |
| Ex 23 | Sodium Alginate: 6% | | Antibac. honey blend: 93% | | | | Opiate: 1% | Cox 2 inhibitors |
| Ex 24 | Sodium Alginate: 6% | | Antibac. honey blend: 92% | | | | Opiate: 0.1% | |
| Ex 25 | Sodium Alginate: 6% | | Antibac. honey blend: 94% | | | | Opiate: 0.5% | |
| Ex 26 | Sodium Alginate: 6% | | Antibac. honey blend: 94% | | | | Opiate: 0.01% | |
| Ex 27 | Sodium Alginate 6 | | Antibac. honey blend: 92% | | | | Opiate: 0.05% | |
| Ex 28 | Sodium Alginate: 6% | | Antibac. honey blend: 94% | | | | Opiate: 0.001% | |
| Ex 29 | Sodium Alginate: 6% | | Antibac. honey blend: 93% | | | | Opiate: 0.005% | |
| Ex 30 | Sodium Alginate: 6% | | Antibac. honey blend: 89% | | | | Lidocaine: 5% | |
| Ex 31 | Sodium Alginate: 6% | | Antibac. honey blend: 84% | | | | Lidocaine: 0.5% | |
| Ex 32 | Sodium Alginate: 6% | | Antibac. honey blend: 84% | | | | Lidocaine: 0.05% | |
| Ex 33 | Sodium Alginate: 6% | | Antibac. honey blend: 91% | | | | Prilocaine: 3% | |
| Ex 34 | Sodium Alginate: 6% | | Antibac. honey blend: 94% | | | | Prilocaine: 0.1% | |
| Ex 35 | Sodium Alginate: 6% | | Antibac. honey blend: 94% | | | | Prilocaine: 0.05% | |
| Ex 36 | Sodium Alginate: 6% | | Antibac. honey blend: 93.8% | | | | Hydrocortisone: 0.2% | |
| Ex 37 | Sodium Alginate: 6% | | Antibac. honey blend: 93.9% | | | | Fluocinolone: 0.1% | |
| Ex 38 | Sodium Alginate: 6% | | Honey from *Eucalyptus marginata* (Jarrah): 84% | | | | Urea: 10% | |
| Ex 39 | Sodium Alginate: 6% | | Antibac. honey blend: 93.9% | | | | T retinoir: 0.1% | |
| Ex 40 | Sodium Alginate: 6% | | Antibac. honey blend 88% | | | | Salicylic Acid: 6% | |
| Ex 41 | Sodium Alginate: 6% | | Antibac. honey blend 69% | | | Petrolatum: 25% | | |
| Ex 42 | Sodium Alginate: 6% | | Antibac. honey blend 93.9% | | | | Naftifine: 0.1% | |
| Ex 43 | Sodium Alginate: 6% | | Antibac. honey blend: 92% | | | | Miconazole: 2% | |
| Ex 44 | Collagen 6% | | Antibac. honey blend: 93.5% | | | | recombinant activated FVII (rFVIIa): 0.5% | |

TABLE 2-continued

Examples of Hydrocolloids Compositions in a Low Water Activity Antimicrobial Matrix.

| Ex No | Hydrocolloid 1 | Hydrocolloid 2 | LWAM | Sequestrant | Excipient | Carrier | Other 1 | Other 2 |
|---|---|---|---|---|---|---|---|---|
| Ex 45 | fibrinogen-impregnated collagen 6% | | Antibac. honey blend 94% | | | | | |
| Ex 46 | Potassium Alginate 7% | | Antibac. honey blend: 92% | | | | Bioflavanoids: 1% | |
| Ex 47 | Potassium Alginate: 8% | | honey blend: 42% | | | purified lanolin: 50% | | |
| Ex 48 | Potassium Alginate: 8% | | Honey from genra *Trigona* bee: 91 | | | | | |
| Ex 49 | Potassium Alginate: 8% | | Honey from genra *Austroplebeia* bee: 92% | | | | | |
| Ex 50 | Potassium Alginate: 8% | | Sat. sugar soln: 92% | | | | | |

The invention claimed is:

1. A composition comprising a low water activity antimicrobial matrix, the antimicrobial matrix comprising finely divided particles of at least one hydrocolloid dispersed within the antimicrobial matrix, wherein said finely divided particles are suspended throughout said matrix.

2. The composition of claim 1 wherein the at least one hydrocolloid is selected from one or more naturally occurring hydrocolloids, semi-synthetic hydrocolloids or synthetic hydrocolloids.

3. The composition of claim 1 wherein the low water activity anti-microbial matrix is selected from one or more of a saturated sugar solution, a honey or mixture of honeys, a honey derivative, or an artificial honey.

4. The composition of claim 1 wherein the at least one hydrocolloid constitutes about 1% to 50% by weight of the composition.

5. The composition of claim 1 wherein the at least one hydrocolloid is selected from one or more of a hydrocolloid of botanica, animal or microbial origin.

6. The composition of claim 1 wherein the low water activity anti-microbial matrix constitutes from about 40 to 96% by weight of the composition.

7. The composition of claim 1 further comprising an excipient.

8. The composition of claim 7 wherein the excipient constitutes from about 0.6% to 12% by weight of the composition.

9. The composition of claim 1 further comprising a sequestrant.

10. The composition of claim 9 wherein the sequestrant constitutes from about 0.01% to 3% by weight of the composition.

11. The composition of claim 7 comprising an excipient and a sequestrant.

12. The composition of claim 1 further comprising a chemical carrier.

13. The composition of claim 1 further comprising at least one surfactant.

14. The composition of claim 12 wherein the carrier is a pharmaceutically or veterinary acceptable, non-toxic substance for delivery of the composition to a patient.

15. The composition of claim 14 wherein the carrier is selected from a topical carrier, or a carrier for internal delivery.

16. The composition of claim 1 further comprising one or more of a non-steroidal anti-inflammatory agent, Cox-2 inhibitor, flavanoid, ancillary anti-microbial agent, analgesic or haemostatic agent.

17. The composition of claim 1 wherein the low water activity antibacterial matrix is a honey.

18. The composition of claim 1 wherein the hydrocolloid is a carbohydrate polymer or salt thereof.

19. The composition of claim 18 wherein the carbohydrate polymer is an alginate or salt thereof.

20. A method of preparing a composition according to claim 1, the method comprising: mixing at least one hydrocolloid with a low water activity matrix, the mixing carried out at a temperature which is below a temperature that will cause degradation of the matrix.

21. The method of claim 20 wherein mixing is carried out with low shear.

22. The method of claim 20 wherein mixing is carried out below about 40° C.

23. The method of claim 21 wherein mixing is carried out at about 25° C.

24. The method of claim 20, further comprising: adding one or both of an excipient and/or a sequestrant to the composition.

25. The method of claim 23 further comprising: combining a chemical carrier and a surfactant by heating and mixing, cooling the mixture of carrier and surfactant until the mixture has a temperature similar to the temperature of the composition; and combining the composition with the mixture of the carrier and surfactant.

26. The method of claim 20 further comprising sterilizing of the composition.

27. The method of claim 25 wherein the composition is sterilized by gamma irradiation at levels between about 25-35 kGy.

28. The method of claim 20 further comprising impregnating a bandage or dressing with the composition for use on a subject.

29. A particulate dispersion of at least one hydrocolloid in a low water activity anti-microbial matrix prepared by the method of claim 20.

30. A method of treating a subject comprising applying a composition of claim 1 to the site of a wound.

31. The composition of claim 1, wherein said finely divided particles are dispersed so that not all of said particles are in direct contact with a wound when said composition is applied to a wound.

* * * * *

UNITED STATES PATENT AND TRADEMARK OFFICE
CERTIFICATE OF CORRECTION

PATENT NO. : 8,632,810 B2  Page 1 of 1
APPLICATION NO. : 12/091897
DATED : January 21, 2014
INVENTOR(S) : Anthony Moloney It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1485 days.

Signed and Sealed this
Twenty-second Day of September, 2015

Michelle K. Lee
*Director of the United States Patent and Trademark Office*